United States Patent
Restrepo et al.

(10) Patent No.: US 9,216,143 B2
(45) Date of Patent: *Dec. 22, 2015

(54) LIQUID PERSONAL CLEANSING COMPOSITION

(71) Applicant: Conopco, Inc., Englewood Cliffs, NJ (US)

(72) Inventors: Nicolas E. Restrepo, Hamden, CT (US); Alexander Kingston Shutak, Fairfield, CT (US); Liang Sheng Tsaur, Norwood, NJ (US); Vivek Subramanian, Southbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/289,703

(22) Filed: May 29, 2014

(65) Prior Publication Data

US 2014/0274865 A1  Sep. 18, 2014

Related U.S. Application Data (63) Continuation of application No. 12/187,793, filed on Aug. 7, 2008, now Pat. No. 8,772,212.

(51) Int. Cl.
| | | |
|---|---|---|
| *A61K 8/00* | (2006.01) | |
| *C11D 3/00* | (2006.01) | |
| *C11D 17/00* | (2006.01) | |

(Continued)

(52) U.S. Cl.
CPC ................ *A61K 8/042* (2013.01); *A61K 8/0291* (2013.01); *A61K 8/0295* (2013.01); *A61K 8/31* (2013.01); *A61Q 5/02* (2013.01); *A61Q 19/10* (2013.01)

(58) Field of Classification Search
CPC ..... A61K 8/02; A61K 8/0241; A61K 8/0295; A61K 8/31; A61K 8/345
USPC .......................... 510/159, 355, 417, 422, 427
See application file for complete search history.

(56) References Cited

U.S. PATENT DOCUMENTS

| | | |
|---|---|---|
| 5,308,526 A | 5/1994 | Dias et al. |
| 5,441,730 A | 8/1995 | Gough |

(Continued)

FOREIGN PATENT DOCUMENTS

| | | |
|---|---|---|
| EP | 0648111 | 5/1999 |
| GB | 1346645 | 2/1974 |

(Continued)

OTHER PUBLICATIONS

Penreco White Petrolatum USP (All Grades) Material Safety Data Sheet, Penreco White Petrolatum USP, Nov. 28, 2006, pp. 1-6 (XP055071581).

(Continued)

*Primary Examiner* — Ling Choi
*Assistant Examiner* — Thuy-Ai Nguyen
(74) *Attorney, Agent, or Firm* — Ronald A. Koatz (57) ABSTRACT

A stable, multiphase liquid isotropic cleansing composition is described that contains high levels of Petrolatum and shows a substantial decrease in reflectance compared with isotropic cleansing compositions containing other oils and liquid crystalline compositions with similar levels of oils. The inventive composition has a total of less than 2% by wt. of other oils such as glyceride, mineral and silicone oils, or blends thereof.

18 Claims, 5 Drawing Sheets

(51) Int. Cl.
*A61K 8/04* (2006.01)
*A61K 8/02* (2006.01)
*A61K 8/31* (2006.01)
*A61Q 19/10* (2006.01)
*A61Q 5/02* (2006.01)

(56) References Cited

U.S. PATENT DOCUMENTS

| | | |
|---|---|---|
| 5,496,488 A | 3/1996 | Kacher |
| 5,532,000 A | 7/1996 | Kauffmann |
| 5,580,550 A | 12/1996 | Gough |
| 5,661,189 A | 8/1997 | Grieveson et al. |
| 5,716,920 A | 2/1998 | Glenn, Jr. |
| 5,851,978 A | 12/1998 | Shana'a |
| 5,854,293 A | 12/1998 | Glenn, Jr. |
| 5,869,070 A | 2/1999 | Dixon |
| 5,965,500 A | 10/1999 | Puvvada |
| 6,001,344 A | 12/1999 | Villa et al. |
| 6,066,608 A * | 5/2000 | Glenn, Jr. .............. 510/159 |
| 6,395,690 B1 | 5/2002 | Tsaur |
| 6,395,691 B1 | 5/2002 | Tsaur |
| 7,084,104 B2 | 8/2006 | Martin et al. |
| 7,098,180 B2 | 8/2006 | Ganopolsky et al. |
| 7,129,201 B2 | 10/2006 | Yang et al. |
| 2002/0034489 A1 | 3/2002 | Wiegland et al. |
| 2004/0116539 A1 | 6/2004 | Biercevicz et al. |
| 2004/0121925 A1 | 6/2004 | Harmakler |
| 2004/0136943 A1 | 7/2004 | Tomokuni |
| 2006/0079421 A1 | 4/2006 | Wagner et al. |
| 2006/0252662 A1 | 11/2006 | Soffin et al. |
| 2007/0135319 A1 | 6/2007 | Wei et al. |

FOREIGN PATENT DOCUMENTS

| | | |
|---|---|---|
| WO | WO9401085 A2 | 1/1994 |
| WO | WO9602224 A1 | 2/1996 |
| WO | WO9617591 A1 | 6/1996 |
| WO | WO9909948 | 3/1999 |
| WO | WO9909950 | 3/1999 |
| WO | WO9962493 | 12/1999 |
| WO | WO0000494 | 1/2000 |
| WO | WO0117500 A1 | 3/2001 |
| WO | WO02067892 A2 | 9/2002 |
| WO | WO2004054693 A1 | 7/2004 |

OTHER PUBLICATIONS

Search Report in EP14176408 dated Apr. 28, 2015.

* cited by examiner

LIQUID PERSONAL CLEANSING COMPOSITION

This application is a continuation of U.S. Ser. No. 12/187,793 filed Aug. 7, 2008.

BACKGROUND OF THE INVENTION

1. Field of the Invention

The present invention relates to liquid cleansing compositions suitable for topical application for cleansing the human body, such as the skin and hair. In particular, it relates to a stable, multiphase isotropic or gel type (hereinafter "isotropic") personal cleansing composition with low reflectance that contains a petrolatum with a specific melting point range as the primary hydrophobic emollient.

2. Background of the Art

Commercially available liquid personal cleansing compositions i.e. shower gels, facial and hand cleansers that are rich in hydrophobic emollient oils are generally applied to simultaneously cleanse and moisturize the skin. Liquid crystalline cleansing compositions can structure substantial quantities of oils but are milky white in appearance which some users find unattractive. Isotropic cleansing compositions are often transparent or otherwise low in reflectance presenting an attractive appearance to many users but disadvantageously cannot structure substantial levels of hydrophobic emollients to yield a stable product for effective skin moisturization. A stable product is defined herein as having no noticeable phase separation under the stability test conditions described below. Surprisingly, a stable, multiphase isotropic structured cleansing composition was discovered that has both an attractive lower reflectance, can also structure substantial levels of petrolatum wherein the petrolatum has a melting point between 35 and 80 C and a minimum viscosity of 10,000 cps at 32 C (hereinafter "Petrolatum") for effective moisturization and wherein the composition must be free of other hydrophobic emollients above specific levels to achieve its attractive appearance and unique Petrolatum particle size distribution.

Isotropic liquid cleansers are known that have hydrophobic emollient oils. U.S. Pat. No. 6,001,344 issued on Dec. 14, 1999 to Villa et al. discloses an isotropic cleansing composition having large oil droplets in the 1 to 500 micron range average diameter.

U.S. Pat. Nos. 5,854,293 and 6,066,608 issued on Dec. 29, 1998 and on May 23, 2000 to Glenn Jr. respectively disclose a moisturizing liquid personal cleansing emulsion with at least 10% of its lipophilic skin moisturizing agent droplets having a diameter of greater than 200 microns. Glenn Jr. further discloses the use of stabilizers selected from crystalline, hydroxyl-containing stabilizers, polymeric thickeners, C10-C18 diesters, amorphous silica or smectite clay.

U.S. Pat. No. 5,965,500 issued on Oct. 12, 1999 to Puvvada discloses a stable, isotropic liquid cleansing composition containing high levels of emollients equal to or in excess of the surfactant level. The composition further contains C2-C24 fatty acids and/or cationic polymers in a preferred embodiment.

U.S. Pat. No. 5,661,189 issued on Aug. 26, 1997 to Grieveson et al. discloses an isotropic, aqueous liquid cleansing and moisturizing composition with a thickened benefit agent having a weight average particle size in the range of 50 to 500 microns and an optional structuring agent selected from clays, fatty acids and derivatives thereof, cross-linked polyacrylates, polyvinylpyrrolidone, natural gums, polysaccharide derivatives, polyols, polyol esters and inorganic salts.

U.S. Pat. No. 7,098,180 issued on Aug. 29, 2006 to Ganopolsky et al. discloses an isotropic cleansing composition containing anionic and amphoteric surfactants, and a hydrophobically modified crosslinked, anionic acrylic copolymer.

U.S. Patent Publication No. 2004/0121925 published on Jun. 24, 2004 to Harmalker discloses a stable isotropic cleansing composition containing anionic and amphoteric surfactants, xanthan and guar gum thickeners, and dispersed phase suspended particles of conditioning agents in the 200-2500 micron diameter range and with a clarity of less than or equal to 20 NTU of the continuous phase absent the particles. The particles consist of gums, gelatins or the like and may contain oil(s) within the particles.

U.S. Pat. No. 7,084,104 issued on Aug. 1, 2006 to Martin et al. discloses an isotropic cleansing composition containing anionic and amphoteric surfactants, a hydrophobically modified crosslinked, anionic acrylic copolymer thickener, volatile silicone conditioners and humectants.

BRIEF DESCRIPTION OF THE INVENTION

In one aspect of the invention is a stable, multiphase isotropic cleansing composition, including but not limited to:

a. about 99 to 84% by wt. of water based on the total composition;

b. about 1 to 16% by wt. of Petrolatum based on the total composition wherein the Petrolatum has a melting point between 35 and 80 C and a minimum viscosity of 10,000 cps at 32 C;

c. wherein an aqueous phase includes about 1 to 25% by wt. of a non-soap anionic surfactant based on the total composition and about 1 to 20% by wt. of an amphoteric surfactant based on the total composition;

d. wherein the aqueous phase contains about 0.5 to 10% by wt. of total polymeric dispersion stabilizing agent(s) based on the total composition;

e. less than about 2% by wt. of total hydrophobic glyceride(s), hydrocarbon(s) excluding Petrolatum, or silicone oils or blends and derivatives thereof based on the total composition; and f. less than about 1.5% by wt. of total liquid crystalline structurant(s), crystalline hydroxyl-containing stabilizer(s), C10-C22 ethylene glycol fatty acid ester(s), silica(s), clay(s) or blends thereof based on the total composition.

In another aspect of the invention is a process of preparing a stable, multiphase isotropic cleansing composition, including but not limited to the steps 2.5 of in no particular order:

a. blending water, surfactant(s), and polymeric dispersion stabilizing agent(s) until uniform to make an oil-free, transparent, isotropic aqueous preblend;

b. feeding the aqueous preblend into a blending tube, the aqueous preblend moving through the blending tube at a rate from about 227 to 113.7 kg (50-250 lbs.) per minute; and c. feeding Petrolatum having a melting point between 35 and 80 C and a minimum viscosity of 10,000 cps at 32 C into the blending tube via a multiport injector (defined as having 2 or more conduit outlets) at a rate sufficient to form a blend with a wt. % ratio range of about 1% Petrolatum to 99% aqueous preblend to about 16% Petrolatum to 84% aqueous preblend.

DETAILED DESCRIPTION OF THE INVENTION

In one aspect of the invention is a stable, multiphase isotropic cleansing composition, including but not limited to:

a. about 99 to 84% by wt. of water based on the total composition;

b. about 1 to 16% by wt. of Petrolatum based on the total composition wherein the Petrolatum has a melting point between 35 and 80 C and a minimum viscosity of 10 Kps at 32 C;

c. wherein an aqueous phase includes about 1 to 25% by wt. of a non-soap anionic surfactant based on the total composition (preferably with a minimum concentration of about 4, 8 or 12% by wt. and a maximum concentration of about 16, 20 or 25% by wt.) and about 1 to 20% by wt. of an amphoteric surfactant based on the total composition (preferably with a minimum concentration of about 2, 4 or 6% by wt. and a maximum concentration of about 12, 16 or 20% by wt.);

d. wherein the aqueous phase contains about 0.5 to 10% by wt. of total polymeric dispersion stabilizing agent(s) based on the total composition (preferably with a minimum concentration of about 1.0, 1.5 or 2% by wt. and a maximum concentration of about 8 or 9% by wt.);

e. less than about 2% by wt. (preferably less than about 1.5. 1 or 0.5% by wt.) of total hydrophobic glyceride(s), hydrocarbon(s) excluding Petrolatum, or silicone oils or blends and derivatives thereof based on the total composition; and f. less than about 1.5% by wt. (preferably less than about 1.0 or 0.5% by wt.) of total liquid crystalline structurant(s), crystalline hydroxyl-containing stabilizer(s), C10-C22 ethylene glycol fatty acid ester(s), silica(s), clay(s), optionally insoluble pigments, or blends thereof based on the total composition.

A stable composition is herein defined as a product where there is no observed phase separation after 3 months at storage temperatures of either 45 C, 37 C, 25 C, or 4 C, or after storage for 2 weeks at 50 C. Preferably the Petrolatum is present in a minimum concentration of about 2.5, 3, 3.5 or 4% by wt. and in a maximum concentration of about 4, 6, 8 or 12% by wt. More preferably the Petrolatum has a maximum viscosity of about 20,000 cps, 35,000 cps or 50,000 cps at 32 C.

In a preferred embodiment the inventive cleansing composition contains only an aqueous and an oil phase. Preferably the cleansing composition has a maximum reflectance of 80% as measured by the standard reflectance method described below. More preferably the maximum reflectance is 70, 60 or 50%.

Advantageously the cleansing composition possesses greater than 50% by volume of the Petrolatum phase particles with a diameter greater than 50, 100, 150 or 200 microns as measured by the standard particle size method. Preferably greater than 90% by volume of the Petrolatum phase particles have a diameter greater than 10, 20, 30 or 40 microns.

In another aspect of the invention is a process of preparing a stable, multiphase isotropic cleansing composition, including but not limited to the steps of in no particular order:

a. blending water, surfactant(s), and polymeric dispersion stabilizing agent(s) until uniform to make an oil-free, transparent, isotropic aqueous preblend;

b. feeding the aqueous preblend into a blending tube, the aqueous preblend moving through the blending tube at a rate from about 22.7 to 113.7 kg (50-250 lbs.) per minute; and c. feeding Petrolatum, having a melting point between 35 and 80 C and a minimum viscosity of 10,000 cps at 32 C. into the blending tube via a multiport injector at a rate sufficient to form a blend with a wt. % ratio range of about 1% Petrolatum to 99% aqueous preblend to about 16% Petrolatum to 84% aqueous preblend. The Petrolatum may be optionally blended with other components to form a Petrolatum preblend prior to feeding the Petrolatum into the aqueous preblend.

Preferably the temperature of the aqueous preblend is adjusted to about 40 C or less (preferably below 35 C and most preferably about 32 C) and the temperature of the Petrolatum is adjusted to 50 to 70 C prior to being blended together. More preferably the Petrolatum is adjusted above 50 C or 55 C and most preferably about 60 C. Most preferably the temperature of the final product after blending does not exceed 37 C.

Advantageously the multiport injector has a minimum of 3, 4, 5, 6, 7, or 8 conduit ports. In a preferred embodiment, the ports of the multipart injector are arranged in a symmetric pattern. Preferably at the terminal points of a 3 or more pointed star oriented normal to the flow of the aqueous preblend and located along the periphery of a mixing conduit. More preferably the ports have a diameter in the range of about 2 to 20 mm with a minimum diameter of about 4, 6 or 8 mm and a maximum diameter of about 18, 16, 14 or 12 mm. Most preferably the diameter is about 9 mm.

Process Description:

The inventive composition is prepared in a preferred embodiment by injection of Petrolatum or an optional non-aqueous preblend thereof into an isotropic aqueous preblend using the process described below and depicted in the process flow diagram of FIG. 1. The Petrolatum preblend consists of Petrolatum and optionally active agents (as defined below) or other optional ingredients which may include particles such as polyethylene or microthene or other particles or blends thereof that can be stably dissolved or suspended in a Petrolatum matrix and which are either not specifically excluded from the invention nor increase the product reflectance beyond 50, 60, 70 or 80 percent. The Petrolatum or Petrolatum preblend, when added to the aqueous preblend via injection under specified flow and temperature conditions, creates a Petrolatum particle size distribution and product skin deposition properties not easily or reproducibly attainable via batch processing. Multi-port injection is used for injecting the Petrolatum preblend in a preferred embodiment and an example of a suitable eight port star-shaped injector 100 is illustrated in FIG. 2. Other multi-port star or non-star shaped symmetric or asymmetric configurations of ports may be advantageously used for dividing the Petrolatum or Petrolatum preblend into multiple streams at the point where the Petrolatum is injected into the aqueous phase.

In another embodiment of the invention, a modified batch process may be used to prepare the isotropic aqueous phase, followed by Petrolatum or a Petrolatum preblend injection with controlled mixing within the batch tank. Over mixing results in opaque product appearance i.e. emulsified (very small) oil droplets whose average diameter is below 50, 30, 10 or 1 micron and is typically in the sub-micron range. Such an over-mixed product will not have the advantageous particle size distribution, reflectance level or product performance attributes of the inventive composition.

The in-line injection embodiment with the use of multi-port injection is seen to achieve more consistent product attributes than batch processing. Another desirable feature observed with the inline injection process illustrated in FIG. 1 are constant flow rates of each of the aqueous and Petrolatum preblend streams both prior to and after mixing at constant pressure. Constant flow rates are seen to minimize product particle size distribution and reflectance variability.

In a preferred embodiment, the Petrolatum preblend tank 20 is hot water jacketed for temperature control and agitator 24 consists of both an offset mixer and a scrape wall mixer.

Multiport Injector 28 functions to subdivide Petrolatum preblend flow and 2.5 break up the oil stream into droplets under specific temperature and flow conditions. The flow of liquid that passes through the injector depends on system pressure, normally the difference in upstream pressure to the injector and discharge pressure (usually atmospheric). For in-line injection, the flow can be calculated as follows:

$$GPM = K(Psig(upstream) - Psig(injector\ outlet))$$

K=constant for specific injector used.

Viscosity of the liquid stream will affect injector performance since generally fluids with viscosities greater than 100 cps (at system temperature) are difficult to atomize except with air. Air is not used for atomization is the inventive process or with the inventive product. Preferably the viscosity range used herein is about 100 to 20,000 cps at the process temperature used (measured e.g. with a Brookfield spindle 5 at 20 rpm) In a preferred embodiment, the eight (8) port star shaped injector depicted in FIG. 2 was observed to allow substantial Petrolatum preblend droplet formation in the range of 100-1000 microns. Other features of this injector include a central orifice 120 surrounded by injector ports 110 on the outlet end of conduit 130. Flange 140 is positioned on the opposite end of conduit 130 and contains a concentric groove (not shown) adapted to receive sealing gasket 160. Conduit 170 has extension conduit 164 and flange 172 connected on a first end and flange 180 connected on a second end. Flange 172 contains a concentric groove 174 adapted to receive sealing gasket 160. Extension conduit 164 is sized to receive ball 150 and be received in conduit 130. In positive flow operation, liquid flows through conduit 170, then through conduits 164 and 130 whereby ball 150 moves to seal the central portion of orifice 120 while still permitting liquid flow through ports 110.

Droplet size formation for single fluid nozzles (non air systems) may be determined by the following equation for a modest change in system pressure (on the order of delta 40 PSIG).

$$D2/D1 = (P2/P1)^{-0.3}$$

Liquid specific gravity is known to affect liquid flow through the injector nozzle. The following relationship exists between fluids with different specific gravities (SG) where Q is given in units of volume/time.

$$Q1/Q2 = (SG1/SG2)^{0.5}$$

A specific increase in viscosity at injection is critical for droplet formation in the inventive process. The aqueous preblend flow (approx. 95% of the total formula) provides the heat capacity necessary to cool the Petrolatum preblend resulting in an increase in viscosity and favoring Petrolatum droplet formation and larger particle sizes.

Figure 1:
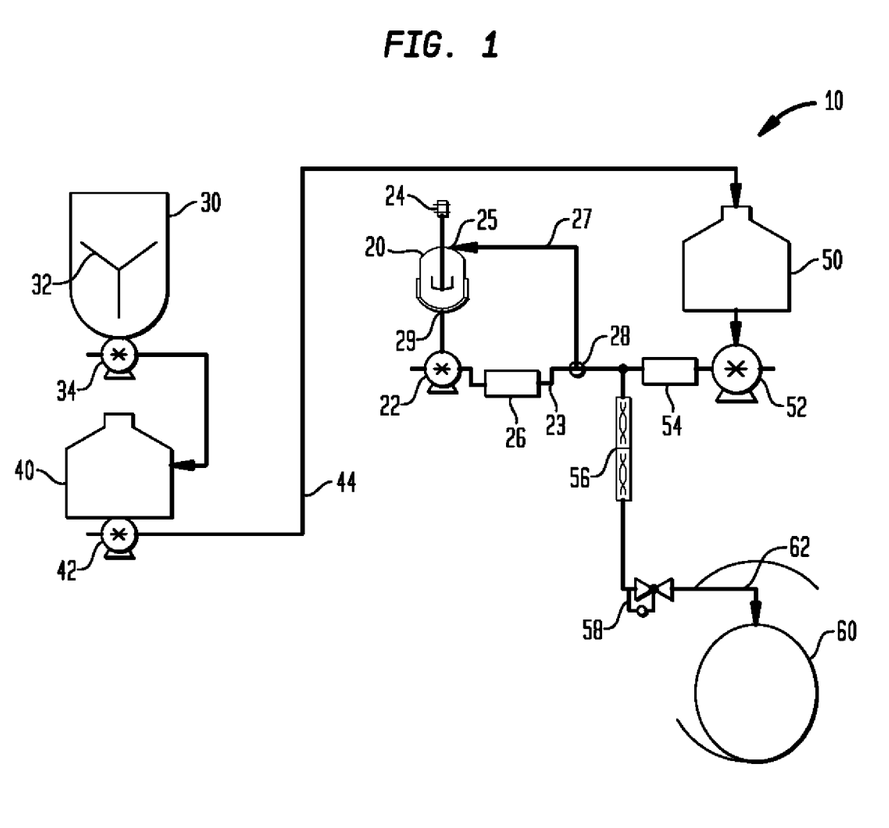
FIG. 1 is a schematic process flow diagram of a preferred embodiment of the inventive process.
Figure 2:
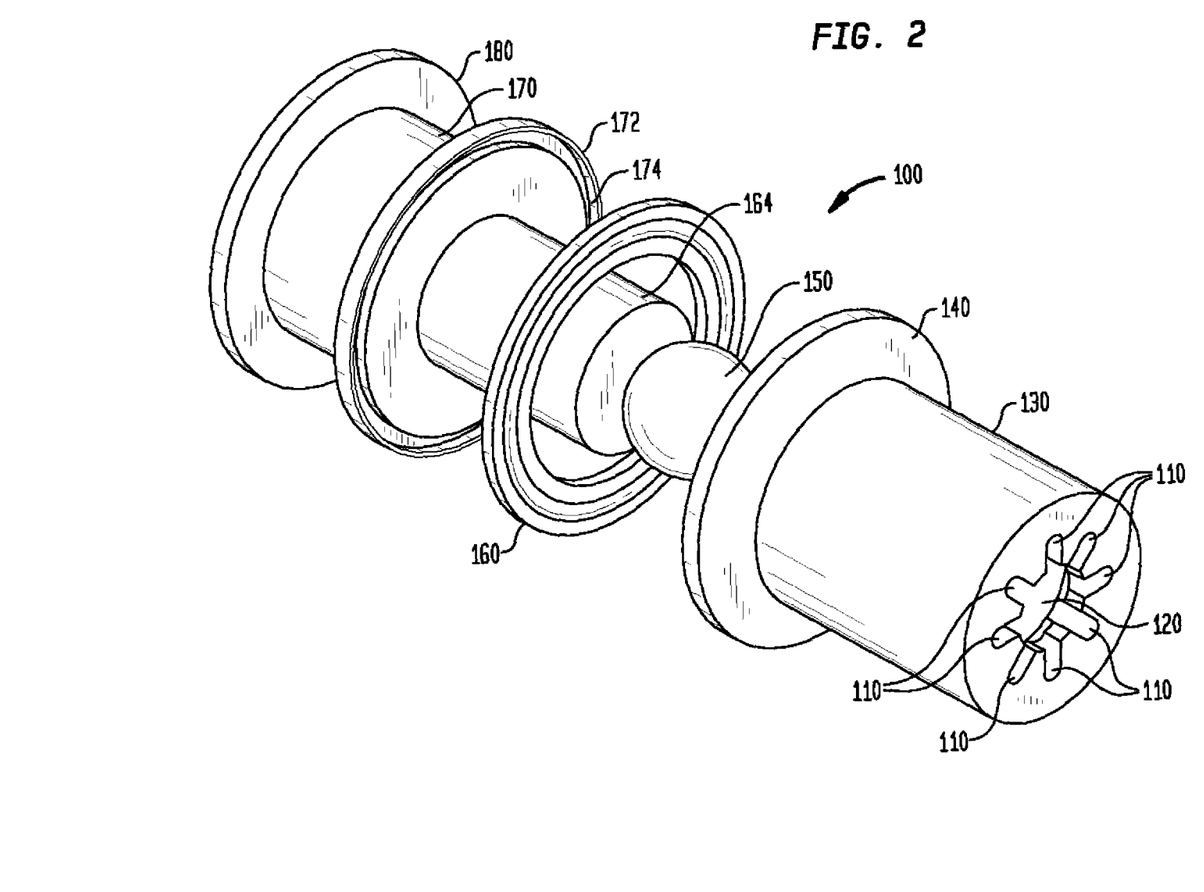
FIG. 2 is a detailed, exploded, perspective view of a preferred embodiment of the multi-port valve 100 illustrated in FIG. 1.

In a preferred embodiment of the process of FIG. 1, static mixers 56 are employed to provide product uniformity i.e. droplet size distribution, regardless of flow rate, viscosity or density profiles. Static mixers 56 contain elements that effectively mix where laminar flow conditions typically exist such as in finished product transfer line 62. Although not wishing to be bound by the following theoretical explanation, it is believed that laminar flow conditions will generate a velocity gradient with maximum velocity at the center of a conventional open conduit. Petrolatum droplets being less dense in aqueous medium will tend to migrate to the maximum velocity area. The mixing elements situated in the center of static mixer 56 will disrupt this velocity gradient and thereby provide more complete final product homogeneity.

For static mixers such as the KMR-SAN6 (Chemineer Corp., Andover, Mass.), (M) is proportional to # of elements (N) according to the following equation:

$$M = 2^N$$

As an example, two (2) static mixers with 6 elements per mixer provided sufficient mixing to achieve inventive product uniformity.

$M = 2^{12}$ or 4096 product stream splits.

Petrolatum preblend Processing Steps (200 kg batch)
1.) Now referring to FIG. 1, set the Petrolatum preblend Tank 20 hot water heater (not shown) to 60 C.
2.) Add 108.8 kg of Petrolatum to tank 20.
3.) Set tank agitator 24 to the following: Turbine—40 Htz Scrapes—0 Htz
4.) Continue to heat Petrolatum preblend to 60 C. When temperature reaches 57-60 C polyethylene beads can optionally be added. Add 38 kg of beads slowly—addition time approximately 2 minutes. As the beads are added increase turbine speed to maximum without splashing oil phase.
5.) After the completion of optional bead addition, set agitation as follows: Turbine—40 Htz Scrapes-Maximum. Mix at these speeds for 2.0 minutes.
6.) After the completion of the 2.0 minute mix change agitator 24 to the following: Turbine—40 Htz Scrapes—80 Htz.
7.) Continue mixing and heating this preblend to 60 C.

Aqueous Base Processing Procedure (4000 Kg Batch).
1.) 1600 kg of deionized water are added to base preparation tank 30 and heated to 55 C.
2.) 240 kg of Carbopol Aqua SF-1 polymer is dissolved in the water with agitation.
3.) 700 kg of a blend of SLES and CMEA (51.4% by wt. SLES, 6.67% CMEA by wt.) with agitation using agitator 32 and blended for 20 minutes at 55 C.
4.) 240.4 kg of Cocamidopropyl Betaine, 2 kg of Tetrasodium EDTA, 39%; 89 kg of deionized water, 6 kg of sodium hydroxide, 50% by wt.; and 925.66 kg of deionized water are added in sequence with agitation until dissolved and the blend is then cooled to 35 to 40 C.
5.) 7.2 kg of DMDM Hydantoin, 55%; 0.72 kg of Colorant Yellow, 40 kg of fragrance and 20 kg. of Captivates HC 01576 (Blue) Yellow beads are next sequentially added and blended until uniform.

Petrolatum preblend injection to base aqueous phase
1.) Open Petrolatum preblend tank recirculation line 27.
2.) Disconnect the Petrolatum preblend recirculation line at the tank top port 25 and place in a waste container.
3.) Open the side mounted Petrolatum preblend Tank valve 29.
4.) Set the Petrolatum preblend Pump 22 to 2.47 lbs/min.
5.) Turn on the Petrolatum preblend pump 22 to purge the line of any water or mineral oil, and then turn off the pump.

6.) Immediately connect the recirculation line 27 to the top of the Petrolatum preblend Tank 20 and turn on the Petrolatum preblend Pump 22. Check to make sure the Petrolatum preblend is recirculating back into the top of the tank 20. Both aqueous and oil phases are now ready to be blended.

7.) Set the Base pump 42 at the desired transfer rate (For a total rate of 50 lbs./min set the base pump 42 to 47.53 lbs./min. Check the Petrolatum preblend pump at the meter to be sure it is recirculating at 2.47 lbs./min.

8.) Filler transfer line 62 should be purged for 3.0 minutes.

9.) Flow rates for both the Base Pump 42 and Petrolatum preblend Pump 22 must be controlled to +/−3% of 47.53 lbs./min and to +/−3% of 2.47 lbs./min respectively.

10.) The temperature of the Petrolatum preblend must be controlled to +/−2 degrees C. with a set point of 60 C and the aqueous base must be 35 C or lower.

11.) The blending pressure (as measured with a pressure gauge immediately after the static mixer elements (56) must be maintained to 32 psi+/−3 psi.

12.) The pump pressure recorded at the output of hold tank pump 42 must be 80 psi or lower.

Surfactants:

Surfactants are an essential component of the inventive cleansing composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The cleansing composition of the present invention contains one or more non-soap anionic detergents. Non-soap anionic surfactants are preferably used at levels as low as 1 or 4, 8 or 12% by wt. and at levels as high as 16, 20 or 25% by wt. Soaps are present at less than 0.1% by wt. and are preferably absent from the inventive cleansing composition due to the requirement that the composition is neutral to slightly acid i.e. that the maximum pH is about 7.0, preferably about 6.8 or more preferably about 6.5. The minimum pH is preferably about 3.5, more preferably about 4.5 and most preferably about 5.5.

The anionic detergent active which may be used in the invention may be aliphatic sulfonates, such as a primary alkane (e.g., $C_8$-$C_{22}$) sulfonate, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or aromatic sulfonates such as alkyl benzene sulfonate. The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$-$C_{22}$ sulfosuccinates); alkyl and acyl taurates, alkyl and acyl sarcosinates, sulfoacetates, $C_8$-$C_{22}$ alkyl phosphates and phosphates, alkyl phosphate esters and alkoxyl alkyl phosphate esters, acyl lactates, $C_8$-$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$-$C_{22}$ alkyl and M is a solubilizing cation.

Sarcosinates are generally indicated by the formula:

$$R^1CON(CH_3)CH_2CO_2M,$$

wherein $R^1$ ranges from $C_8$-$C_{20}$ alkyl and M is a solubilizing cation.

Taurates are generally identified by formula:

$$R^2CONR^3CH_2CH_2SO_3M$$

wherein $R^2$ ranges from $C_8$-$C_{20}$ alkyl, $R^3$ ranges from $C_1$-$C_4$ alkyl and M is a solubilizing cation.

The inventive cleansing composition may contain $C_8$-$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

$$RC-O(O)-C(X)H-C(Y)H_2-(OCH-CH_2)_m-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric Surfactants

One or more amphoteric surfactants are used in this invention. Amphoteric surfactants are preferably used at levels as low as 2, 4, or 6% by wt. and at levels as high as 12, 16 or 20% by wt. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-[-C(O)-NH(CH_2)_n-]_m-N^+-(R^2)(R^3)X-Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is $-CO_2-$ or $-SO_3-$

Suitable amphoteric surfactants within the above general formula include simple betaines of formula:

$$R^1-N^+-(R^2)(R^3)CH_2CO_2^-$$

and amido betaines of formula:

$$R^1-CONH(CH_2)_n-N^+-(R^2)(R^3)CH_2CO_2^-$$

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1—N^+—(R^2)(R^3)(CH_2)_3SO_3^-$$

Or $$R^1CONH(CH_2)_m—N^+—(R^2)(R^3)(CH_2)_3SO_3^-$$

where m is 2 or 3, or variants of these in which —(CH$_2$)$_3$SO$_3^-$ is replaced by $$—CH_2C(OH)(H)CH_2SO_3^-$$

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

The combination of total non-soap anionic, nonionic, amphoteric surfactants and polymeric dispersion stabilizing agents(s) (discussed below) should preferably be about 5 to 30% by wt. of the composition.

Nonionic Surfactants

One or more nonionic surfactants may be used in the cleansing composition of the present invention. Nonionic surfactants are preferably used at levels as low as 0.5, 1, 1.5 or 2% by wt. and at levels as high as 6, 8, 10 or 12% by wt. The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$-$C_{22}$) phenols ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

Preferred nonionic surfactants include fatty acid/alcohol ethoxylates having the following structures
a) HOCH2(CH2)n(CH2CH2O)xH or
b) HOOC(CH2)m(CH2CH2O)yH;
where m, n are independently <18; and x, y are independently >1. preferably m, n are independently 6 to 18; x, y are independently 1 to 30;
c) HOOC(CH2)i-CH=CH—(CH2)k(CH2CH2O)zH;
where i, k are independently 5 to 15; and z is independently 5 to 50. preferably i, k are independently 6 to 12; and z is independently 15 to 35.

The nonionic may also include a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

A useful component in compositions according to the invention is a cationic skin feel agent or polymer, such as for example cationic celluloses. Cationic polymers are preferably used at levels as low as about 0.1 to 2% up to levels as high as the solubility limit of the specific polymer, or preferably up to about 4 to 5% by wt., provided that the solubility limit of the particular cationic polymer or blend thereof is not exceeded.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially JAGUAR C13S, and JAGUAR C-14/BFG. The JAGUAR C14/BFG material is the same molecule as JAGUAR C13, except that a glyoxal cross linker has replaced the boron. Other cationic skin feel agents known in the art may be used provided that they are compatible with the inventive formulation.

Other suitable examples of surfactants described above which may be used are described in "Surface Active Agents and Detergents" (Vol. I & II) by Schwartz, Perry & Berch, incorporated into the subject application by reference in its entirety.

In addition, the inventive cleansing composition of the invention may include 0 to 15% by wt. optional ingredients as follows: perfumes; sequestering agents, such as tetrasodium ethylenediaminetetraacetate (EDTA), EHDP or mixtures in an amount of 0.01 to 1%, preferably 0.01 to 0.05%; and soluble coloring agents, and the like; all of which are useful in enhancing the appearance or cosmetic properties of the product.

The compositions may further comprise antimicrobials such as 2-hydroxy-4,2',4' trichlorodiphenylether (DP300); preservatives such as dimethyloldimethylhydantoin (Glydant XL1000), parabens, sorbic acid etc., and the like.

The compositions may also comprise coconut acyl mono- or 2.5 diethanol amides as suds boosters, and strongly ionizing salts such as sodium chloride and sodium sulfate may also be used to advantage. Preferably strongly ionizing salts, otherwise known as electrolytes, will be present at less than 3, 2 or 1% by wt.

Antioxidants such as, for example, butylated hydroxytoluene (BHT) and the like may be used advantageously in amounts of about 0.01% or higher if appropriate.

Emollients

The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Moisturizers that also are Humectants such as polyhydric alcohols, e.g. glycerin and propylene glycol, and the like; and polyols such as the polyethylene glycols and the like may be used as hydrophilic emollients. Humectants are preferably used at levels as low as 1, 3 or 5% by wt. and at levels as high as 6, 8 or 10% by wt.

Petrolatum is used in the invention, preferably at levels as low as 1, 3 or 4% by wt. and at levels as high as 5, 6, 8, 12 or 16% by wt. Petrolatum is defined as a mixture of liquid hydrocarbons derived from petroleum having a melting point between 35 and 80 C (as determined by ASTM D127-08, "Standard Test Method for Drop Melting Point of Petroleum Wax, including Petrolatum", ASTM International, West Conshohocken, Pa.) and a minimum viscosity of 10 Kps at 32 C. Preferably it has a viscosity range of 10 to 35 Kps at 32 C. More preferably the upper limit of viscosity is 25 or 50 Kps at 32 C.

Other non-Petrolatum hydrophobic emollients are preferably present at total levels of less than about 1.5, 1.0, or 0.5% by wt. in the inventive composition and are more preferably absent from the composition. These hydrophobic emollients include but are not limited to the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) non-Petrolatum hydrocarbons such as polybutene, liquid paraffins, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) mixtures of any of the foregoing components, and the like.

Isotropic Micellar Phase Compositions:

The inventive cleansing composition possesses isotropic micellar phase microstructure. The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like or discoidal), spherocylindrical, or ellipsoidal micelles may form. As surfactant concentration increases, ordered liquid crystalline phases such as lamellar phase, hexagonal phase, cubic phase or L3 sponge phase may form. The non-isotropic hexagonal phase, consists of long cylindrical micelles arranged in a hexagonal lattice. In general, the microstructure of most personal care products consist of either an isotropic dispersion including spherical micelles; and rod micelles; or an ordered liquid crystalline phase such as a lamellar dispersion.

As noted above, micelles may be spherical or rod-like. Formulations having spherical micelles tend to have a low viscosity and exhibit Newtonian shear behavior (i.e., viscosity stays constant as a function of shear rate; thus, if easy pouring of product is desired, the solution is less viscous. In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means that the product is more difficult to pour).

Lamellar and other liquid crystalline dispersions are not part of the invention. Such dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

One way of characterizing isotropic micellar dispersions (hereinafter "isotropic compositions") include cone and plate viscosity measurement as described below. The inventive isotropic composition has a viscosity in the range of about 500 to about 300,000 cps @ 1/sec shear rate at 25 C as measured by a cone and plate technique described below. Preferably the viscosity is in the range of about 1,000 to 20,000 cps at 25 C.

Polymeric Dispersion Stabilizing Agent(S):

Water soluble or dispersible polymeric dispersion agents are included in the inventive composition. Suitable agents include carbohydrate gums such as cellulose gum, microcrystalline cellulose, cellulose gel, hydroxyethyl cellulose, hydroxypropyl cellulose, sodium carboxymethylcellulose, hydroxymethyl carboxymethyl cellulose, carrageenan, hydroxymethyl carboxypropyl cellulose, methyl cellulose, ethyl cellulose, guar gum, gum karaya, gum tragacanth, gum arabic, gum acacia, gum agar, xanthan gum and mixtures thereof.

Preferred carbohydrate gums are Hydroxypropyl Methocellulose such as Methocel® 40-100 and Methocel 40-202 (Dow Chemicals, Midland, Mich.), Sodium Hydroxypropyl starch phosphate such as Pure-Gel B990 (Grain Processing Corp., Muscatine, Iowa), and Xanthan Gum such as Keltrol CG (CPKelco, Atlanta, Ga.).

Suitable polymeric dispersion agents also include acrylate containing homo and copolymers such as the crosslinked poly acrylates available 2.5 under the CARBOPOL trade name, the hydrophobically modified cross linked polyacrylates available under the AQUA trade name, and the PEMULEN trade name (all sold by Lubrizol Company, Wickliffe, Ohio) and the alkali swellable acrylic latex polymers sold by Rohm and Haas (Philadelphia, Pa.) under the ARYSOL or ACULYN trade names. Preferred acrylates are the Aqua SF-1® and Carbopol Ultrez 21® polymers.

Liquid Crystalline, Clay and Silica Structuring Agents:

Structuring agent(s) that assist in the formation of liquid crystalline network structures such as a lamellar structure as discussed above and insoluble agents such as clays and silicas, that form or assist in forming colloidal or other networks in surfactant solutions, are present at less than 1.5, 1 or 0.5% by wt. total concentration and preferably are not present in the inventive composition. Excluded liquid crystalline structuring agents include but are not limited to saturated $C_{14}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to $C_{30}$ monoglycerol ethers, saturated $C_{16}$ to $C_{30}$ hydroxy fatty acids, $C_{14}$ to $C_{30}$ hydroxylated and nonhydroxylated saturated fatty acids, $C_{14}$ to $C_{30}$ saturated ethoxylated fatty acids, amines and alcohols containing from about 1 to about 5 moles of ethylene oxide diols, $C_{14}$ to $C_{30}$ saturated glyceryl mono esters with a monoglyceride content of at least 40%, $C_{14}$ to $C_{30}$ saturated polyglycerol esters having from about 1 to about 3 alkyl group and from about 2 to about 3 saturated glycerol units, $C_{14}$ to $C_{30}$ glyceryl mono ethers, $C_{14}$ to $C_{30}$ sorbitan mono/diesters, $C_{14}$ to $C_{30}$ saturated ethoxylated sorbitan mono/diesters with about 1 to about 5 moles of ethylene oxide, $C_{14}$ to $C_{30}$ saturated methyl glucoside esters, $C_{14}$ to $C_{30}$ saturated sucrose mono/diesters, $C_{14}$ to $C_{30}$ saturated ethoxylated methyl glucoside esters with about 1 to about 5 moles of ethylene oxide, $C_{14}$ to $C_{30}$ saturated polyglucosides having an average of between 1 to 2 glucose units and mixtures thereof. The foregoing structuring agent(s) include those having an HLB of from about 1 to about 8 and having a melting point of at least about 45° C.

Additional examples of comparative liquid crystalline structuring agents include but are not limited to stearic acid, palmitic acid, stearyl alcohol, cetyl alcohol, behenyl alcohol, stearic acid, palmitic acid, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. Also included are stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Other comparative liquid crystalline structuring agents include but are not limited to crystalline, hydroxyl-containing stabilizers such as a hydroxyl-containing fatty acid, fatty ester or fatty soap water-insoluble wax-like substance or the like.

For example, the crystalline, hydroxy containing stabilizer may be selected from the group consisting of:

(i) $CH_2(OR_1)CH_2(OR_2)CH_2(OR_3)$
Wherein $R_1$ is $—COR_4(CHOH)_xR_5(CHOH)_yR_4$;
wherein
$R_1$ is $—C—R_4(CHOH)_xR_5(CHOH)_yR_6$;
$R_2$ is $R_1$ or H
$R_3$ is $R_1$ or H
$R_4$ is $C_{0-20}$Alkyl
$R_5$ is $C_{0-20}$Alkyl,
$R_6$ is $C_{0-20}$Alkyl
$R_4+R_5+R_6=C_{10-22}$
and wherein $1<=x+y<=4$;
(ii) $R_7COOM$
wherein
$R_7$ is $—R_4(CHOH)_xR_5(CHOH)_yR_6$
M is $Na^+$, $K^+$ or $Mg^{++}$, or H; and
iii) mixtures thereof;

Other comparative hydroxyl-containing stabilizers include but are not limited to 12-hydroxystearic acid, 9,10-dihydroxystearic acid, tri-9,10-dihydroxystearin and tri-12-hydroxystearin (hydrogenated castor oil is mostly tri-12-hydroxystearin).

Also included in this class of comparative structurants are C10-C22 ethylene glycol fatty acid esters.

As discussed above, clay, silica and other particle based comparative structuring agent(s) are present at less than 1.5, 1 or 0.5% by wt. and preferably are not present in the inventive composition. These agents include but are not limited to dispersed amorphous silica selected from the group consisting of fumed silica and precipitated silica and mixtures thereof. As used herein the term "dispersed amorphous silica" refers to small, finely divided non-crystalline silica having a mean agglomerate particle size of less than about 100 microns.

Other examples of comparative structurants include but are not limited to dispersed smectite clay including bentonite and hectorite and mixtures thereof. Bentonite is a colloidal aluminum clay sulfate. Hectorite is a clay containing sodium, magnesium, lithium, silicon, oxygen, hydrogen and fluorine.

Optional Active Agents

Advantageously, active agents other than conditioning agents such as emollients or moisturizers defined above may be added to the cleansing composition in a safe and effective amount during formulation to treat the skin during the use of the product provided that they do not exceed solubility limits whereby the reflectance increases beyond 80% in the cleansing composition. Suitable active ingredients include those that are soluble in the aqueous phase, in the Petrolatum phase or in both phases. Suitable active agents may be advantageously selected from antimicrobial and antifungal actives, vitamins, anti-acne actives; anti-wrinkle, anti-skin atrophy and skin repair actives; skin barrier repair actives; non-steroidal cosmetic soothing actives; artificial tanning agents and accelerators; skin lightening actives; sunscreen actives; sebum stimulators; sebum inhibitors; anti-oxidants; protease inhibitors; skin tightening agents; anti-itch ingredients; hair growth inhibitors; 5-alpha reductase inhibitors; desquamating enzyme enhancers; anti-glycation agents; topical anesthetics, or mixtures thereof; and the like.

These active agents may be selected from water soluble active agents, oil soluble active agents, pharmaceutically-acceptable salts and mixtures thereof. Advantageously the agents will be soluble or dispersible in the cleansing composition. The term "active agent" as used herein, means personal care actives which can be used to deliver a benefit to the skin and/or hair and which generally are not used to confer a conditioning benefit, as is conferred by humectants and emollients previously described herein. The term "safe and effective amount" as used herein, means an amount of active agent high enough to modify the condition to be treated or to deliver the desired skin care benefit, but low enough to avoid serious side effects. The term "benefit," as used herein, means the therapeutic, prophylactic, and/or chronic benefits associated with treating a particular condition with one or more of the active agents described herein. What is a safe and effective amount of the active agent ingredient will vary with the specific active agent, the ability of the active to penetrate through the skin, the age, health condition, and skin condition of the user, and other like factors. Preferably the composition of the present invention comprise from about 0.01% to about 50%, more preferably from about 0.05% to about 25%, even more preferably 0.1% to about 10%, and most preferably 0.1% % to about 5%, by weight of the active agent component.

Anti-acne actives can be effective in treating acne vulgaris, a chronic disorder of the pilosebaceous follicles. Nonlimiting examples of useful anti-acne actives include the keratolytics such as salicylic acid (o-hydroxybenzoic acid), derivatives of salicylic acid such as 5-octanoyl salicylic acid and 4 methoxysalicylic acid, and resorcinol; retinoids such as retinoic acid and its derivatives (e.g., cis and trans); sulfur-containing D and L amino acids and their derivatives and salts, particularly their N-acetyl derivatives, mixtures thereof and the like.

Antimicrobial and antifungal actives can be effective to prevent the proliferation and growth of bacteria and fungi. Nonlimiting examples of antimicrobial and antifungal actives include b-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, triclosan; triclocarban; and mixtures thereof and the like.

Anti-wrinkle, anti-skin atrophy and skin repair actives can be effective in replenishing or rejuvenating the epidermal layer. These actives generally provide these desirable skin care benefits by promoting or maintaining the natural process of desquamation. Nonlimiting examples of antiwrinkle and anti-skin atrophy actives include vitamins, minerals, and skin nutrients such as milk, vitamins A, E, and K; vitamin alkyl esters, including vitamin C alkyl esters; magnesium, calcium, copper, zinc and other metallic components; retinoic acid and its derivatives (e.g., cis and trans); retinal; retinol; retinyl esters such as retinyl acetate, retinyl palmitate, and retinyl propionate; vitamin B 3 compounds (such as niacinamide and nicotinic acid), alpha hydroxy acids, beta hydroxy acids, e.g. salicylic acid and derivatives thereof (such as 5-octanoyl salicylic acid, heptyloxy 4 salicylic acid, and 4-methoxy salicylic acid); mixtures thereof and the like.

Skin barrier repair actives are those skin care actives which can help repair and replenish the natural moisture barrier function of the epidermis. Nonlimiting examples of skin barrier repair actives include lipids such as cholesterol, ceramides, sucrose esters and pseudo-ceramides as described in European Patent Specification No. 556,957; ascorbic acid; biotin; biotin esters; phospholipids, mixtures thereof, and the like.

Non-steroidal cosmetic soothing actives can be effective in preventing or treating inflammation of the skin. The soothing active enhances the skin appearance benefits of the present invention, e.g., such agents contribute to a more uniform and acceptable skin tone or color.

Nonlimiting examples of cosmetic soothing agents include the following categories: propionic acid derivatives; acetic acid derivatives; fenamic acid derivatives; mixtures thereof and the like. Many of these cosmetic soothing actives are described in U.S. Pat. No. 4,985,459 to Sunshine et al., issued Jan. 15, 1991, incorporated by reference herein in its entirety.

Artificial tanning actives can help in simulating a natural suntan by increasing melanin in the skin or by producing the appearance of increased melanin in the skin. Nonlimiting examples of artificial tanning agents and accelerators include dihydroxyacetone; tyrosine; tyrosine esters such as ethyl tyrosinate and glucose tyrosinate; mixtures thereof, and the like.

Skin lightening actives can actually decrease the amount of melanin in the skin or provide such an effect by other mechanisms. Nonlimiting examples of skin lightening actives useful herein include aloe extract, alpha-glyceryl-L-ascorbic acid, aminotyroxine, ammonium lactate, glycolic acid, hydroquinone, 4 hydroxyanisole, mixtures thereof, and the like.

Also useful herein are sunscreen actives. A wide variety of sunscreen agents are described in U.S. Pat. No. 5,087,445, to Haffey et al., issued Feb. 11, 1992; U.S. Pat. No. 5,073,372, to Turner et al., issued 2.5 Dec. 17, 1991; U.S. Pat. No. 5,073, 371, to Turner et al. issued Dec. 17, 1991; and Segarin, et al., at Chapter VIII, pages 189 et seq., of Cosmetics Science and Technology, all of which are incorporated herein by reference in their entirety. Nonlimiting examples of sunscreens which are useful in the compositions of the present invention are those selected from the group consisting of octyl methoxyl cinnamate (Parsol MCX) and butyl methoxy benzoylmethane (Parsol 1789), 2-ethylhexyl p-methoxycinnamate, 2-ethylhexyl N,N-dimethyl-p-aminobenzoate, p-aminobenzoic acid, 2-phenylbenzimidazole-5-sulfonic acid, oxybenzone, mixtures thereof, and the like.

Sebum stimulators can increase the production of sebum by the sebaceous glands. Nonlimiting examples of sebum stimulating actives include bryonolic acid, dehydroetiandrosterone (DHEA), orizanol, mixtures thereof, and the like.

Sebum inhibitors can decrease the production of sebum by the sebaceous glands. Nonlimiting examples of useful sebum inhibiting actives include aluminum hydroxy chloride, corticosteroids, dehydroacetic acid and its salts, dichlorophenyl imidazoldioxolan (available from Elubiol), mixtures thereof, and the like.

Also useful as actives in the present invention are protease inhibitors. Protease inhibitors can be divided into two general classes: the proteinases and the peptidases. Proteinases act on specific interior peptide bonds of proteins and peptidases act on peptide bonds adjacent to a free amino or carboxyl group on the end of a protein and thus cleave the protein from the outside. The protease inhibitors suitable for use in the present invention include, but are not limited to, proteinases such as serine proteases, metalloproteases, cysteine proteases, and aspartyl protease, and peptidases, such as carboxypepidases, dipeptidases and aminopepidases, mixtures thereof and the like.

Other useful as active ingredients in the present invention are skin tightening agents. Nonlimiting examples of skin tightening agents which are useful in the compositions of the present invention include monomers which can bind a polymer to the skin such as terpolymers of vinylpyrrolidone, (meth)acrylic acid and a hydrophobic monomer comprised of long chain alkyl (meth)acrylates, mixtures thereof, and the like.

Active ingredients in the present invention may also include anti-itch ingredients. Suitable examples of anti-itch ingredients which are useful in the compositions of the present invention include hydrocortisone, methdilizine and trimeprazineare, mixtures thereof, and the like.

Nonlimiting examples of hair growth inhibitors which are useful in the compositions of the present invention include 17 beta estradiol, anti angiogenic steroids, curcuma extract, cycloxygenase inhibitors, evening primrose oil, linoleic acid and the like. Suitable 5-alpha reductase inhibitors such as ethynylestradiol and genistine mixtures thereof, and the like.

Nonlimiting examples of desquamating enzyme enhancers which are useful in the compositions of the present invention include alanine, aspartic acid, N methyl serine, serine, trimethyl glycine, mixtures thereof, and the like.

A nonlimiting example of an anti-glycation agent which is useful in the compositions of the present invention would be Amadorine (available from Barnet Products Distributor), and the like.

The invention will now be described in greater detail by way of the following non-limiting examples. The examples are for illustrative purposes only and not intended to limit the invention in any way. Physical test methods are described below:

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

All percentages in the specification and examples are intended to be by weight unless stated otherwise.

Example 1

The effect of mixing intensity and aqueous base temperature on reflectance and particle size was studied for compositions having 2, 4, 6 and 8% by wt. respectively of Petrolatum (Inventive Samples A-D). The samples were prepared according to the procedures listed below. Tables 1A and 2A list the reflectance of samples prepared with low intensity mixing. Similarly, Tables 1B and 2B list the particle size of samples prepared with high intensity mixing (200 rpm). The composition of samples A-D is shown in Table 3. Compositions A-D were found to provide generally low reflectance and relatively large average particle size compared to the comparative example(s) shown in Example 2 below.

TABLE 1A

Reflectance (%)

| Base Temp. | A | B | C | D |
|---|---|---|---|---|
| 43.3 C. | 45.57 | 54.77 | 57.49 | 61.87 |
| 37.8 C. | 45.12 | 50.54 | 53.77 | 50.17 |
| 32.2 C. | 45.02 | 43.66 | 44.03 | 45.08 |

TABLE 1B

Particle Size (microns)

| | Sample | | | | | |
|---|---|---|---|---|---|---|
| Base | A | | | B | | |
| Temp. | d(0.1) | d(0.5) | d(0.9) | d(0.1) | d(0.5) | d(0.9) |
| 43.3 C. | 13.08 | 53.93 | 113.68 | 15.7 | 47.95 | 316.74 |
| 37.8 C. | 6.58 | 105.34 | 665.2 | 16.86 | 65.93 | 532.11 |
| 32.2 C. | 2.79 | 94.3 | 861.9 | 2.85 | 74.85 | 639.97 |

| | Sample | | | | | |
|---|---|---|---|---|---|---|
| Base | C | | | D | | |
| Temp | d(0.1) | d(0.5) | d(0.9) | d(0.1) | d(0.5) | d(0.9) |
| 43.3 C. | 17.31 | 56.86 | 224.72 | 22.53 | 55.18 | 149.26 |
| 37.8 C. | 12.78 | 53.07 | 411.61 | 33.18 | 204.6 | 1031.88 |
| 32.2 C. | 3.18 | 102.89 | 692.34 | 45.35 | 308.9 | 1011.31 |

Notes:
d(0.1) means 10% by volume of particles are smaller and 90% by volume of particles are larger.
d(0.5) means 50% by volume of particles are smaller and 50% by volume of particles are larger.
d(0.9) means 90% by volume of particles are smaller and 10% by volume of particles are larger.

TABLE 2A

Reflectance (%)

| Base Temp. | A | B | C | D |
|---|---|---|---|---|
| 43.3 C. | 46.85 | 58.07 | 66.46 | 68.13 |
| 37.8 C. | 50.29 | 53.48 | 51.56 | 58.53 |
| 32.2 C. | 44.63 | 43.52 | 46.26 | 50.88 |

TABLE 2B

Particle Size (microns)

| Base | A | | | B | | |
|---|---|---|---|---|---|---|
| Temp. | d(0.1) | d(0.5) | d(0.9) | d(0.1) | d(0.5) | d(0.9) |
| 43.3 C. | 16.16 | 71.6 | 481.62 | 16.35 | 57.41 | 233.34 |
| 37.8 C. | 17.12 | 55.61 | 254.54 | 19.06 | 74.97 | 693.42 |
| 32.2 C. | 6.15 | 102.68 | 973.39 | 52.13 | 414.43 | 1026.47 |

| Base | C | | | D | | |
|---|---|---|---|---|---|---|
| Temp | d(0.1) | d(0.5) | d(0.9) | d(0.1) | d(0.5) | d(0.9) |
| 43.3 C. | 13.01 | 38.6 | 93.22 | 17.48 | 48.91 | 110.64 |
| 37.8 C. | 22.82 | 122.13 | 609.97 | 19.17 | 67.8 | 406.55 |
| 32.2 C. | 80.66 | 387.82 | 989.47 | 46.76 | 284.73 | 862.28 |

TABLE 3

Concentration (% by wt.)

| Component | A | B | C | D |
|---|---|---|---|---|
| SLES (1) | 9.00 | 9.00 | 9.00 | 9.00 |
| CMEA (2) | 1.15 | 1.15 | 1.15 | 1.15 |
| Cocamidopropyl Betaine | 1.70 | 1.70 | 1.70 | 1.70 |
| Acrylate Copolymer (3) | 1.8 | 1.8 | 1.8 | 1.8 |
| Sodium Hydroxide | 0.1 | 0.1 | 0.1 | 0.1 |
| Petrolatum (4) | 2 | 4 | 6 | 8 |
| Fragrance | 1 | 1 | 1 | 1 |
| Preservatives, others (5) | 2 | 2 | 2 | 2 |
| Water | q.s. to 100 | q.s. to 100 | q.s. to 100 | q.s. to 100 |

Notes:
(1) Sodium Laureth Sulfate (Steol CS170, Stepan, Northfield, Illinois)
(2) Cocamide MEA (Mackamide MEA, McIntyre Group, University Park, Illinois)
(3). Aqua SF-1, Lubrizol, Wickliffe, Ohio
(4) Snow White Petrolatum, Penreco (Woodlands, Texas), melting point 51.67 to 57.22° C. (125/135° F.), Viscosity 28.8 Kps Brookfield, Spindle 5, 20 rpm @ 32 C.
(5) includes colors, active agents, beads, etc.

Example 2

Comparative cleansing compositions E-K were formulated according to Table 4 using the procedure listed below and their reflectance were measured and compared to inventive sample B1. Sample B1 is identical in composition to sample B shown in example 1 and is prepared the same way except that an aqueous base temperature of 32.2 C was used when the aqueous base was added to the oil phase. The comparative formulas included C12 and 018 fatty acids (i.e. E and F), and non-Petrolatum oils which are outside the definition of Petrolatum (i.e. G to K). All the comparative examples showed substantially greater reflectance than B1.

TABLE 4

| Component | B1 | E | F | G | H | I | J | K |
|---|---|---|---|---|---|---|---|---|
| | Concentration (% by wt.) | | | | | | | |
| SLES (1) | 9.00 | 9.00 | 9.00 | 9.00 | 9.00 | 9.00 | 9.00 | 9.00 |
| CMEA (2) | 1.15 | 1.15 | 1.15 | 1.15 | 1.15 | 1.15 | 1.15 | 1.15 |
| Cocamidopropyl Betaine | 1.70 | 1.70 | 1.70 | 1.70 | 1.70 | 1.70 | 1.70 | 1.70 |
| Acrylate Copolymer (3) | 1.8 | 1.8 | 1.8 | 1.8 | 1.8 | 1.8 | 1.8 | 1.8 |
| Sodium Hydroxide | 0.1 | 0.1 | 0.1 | 0.1 | 0.1 | 0.1 | 0.1 | 0.1 |
| Lauric Acid | 0 | 4 | 0 | 0 | 0 | 0 | 0 | 0 |
| Stearic Acid | 0 | 0 | 4 | 0 | 0 | 0 | 0 | 0 |
| Mineral Oil | 0 | 0 | 0 | 4 | 0 | 0 | 0 | 0 |
| Soybean Oil | 0 | 0 | 0 | 0 | 4 | 0 | 0 | 0 |
| Carnauba Wax (4) | 0 | 0 | 0 | 0 | 0 | 4 | 0 | 0 |
| Versagel M 500 (5) | 0 | 0 | 0 | 0 | 0 | 0 | 4 | 0 |
| Petrolatum (6) | 4 | 0 | 0 | 0 | 0 | 0 | 0 | 0 |
| Petrolatum Jelly White (7) | 0 | 0 | 0 | 0 | 0 | 0 | 0 | 4 |
| Fragrance | 1 | 1 | 1 | 1 | 1 | 1 | 1 | 1 |
| Preservatives, others (8) | 2 | 2 | 2 | 2 | 2 | 2 | 2 | 2 |
| Water | q.s. to 100 | q.s. to 100 | q.s. to 100 | q.s. to 100 | q.s. to 100 | q.s. to 100 | q.s. to 100 | q.s. to 100 |
| Reflectance (%) | 44.03 | 64.96 | 60.01 | 71.65 | 75.65 | 63.56 | 56.47 | 73.87 |

Notes:
(1) Sodium Laureth Sulfate (Steol CS170, Stepan, Northfield, Illinois)
(2) Mackamide MEA (McIntyre, University Park, Illinois)
(3) Aqua SF-1, Lubrizol (Wickliffe, Ohio)
(4) Carnauba Wax (Rita Corporation, Crystal Lake, Illinois)
(5) Mineral Oil thickened with Ethylene/Propylene/Styrene Copolymer & Butylene/Ethylene/Styrene copolymer (Penreco, Woodlands, Texas)
(6) Snow White Petrolatum USP (Penreco)
(7) Protopet Liquid petrolatum (Sonneborn, Mahwah, NJ) melting point 46.67 C. (116 F.) and viscosity of 740 cps at 32 C. (Brookfield, Spindle 5, 20 rpm @ 32 C.).
(8) includes colors, active agents, beads, etc.

Example 3

Figure 3:
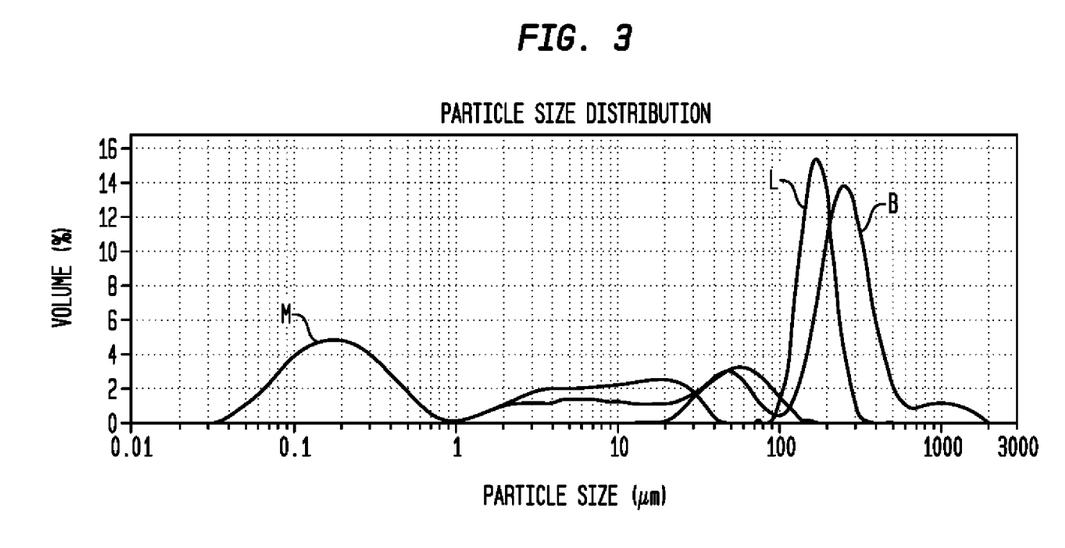
FIG. 3 is a graphical representation of the particle size distribution of particles in a control sample M, an inventive sample B and a comparative sample L described in example 3.

Comparative example L and control M were formulated according to Table 5 below and their reflectance and particle size distribution was measured compared to inventive composition B and illustrated in FIG. 3. Example B was made via the in-line injection process shown in FIG. 1. Example L is made by a conventional batch process described below and contains soybean oil and liquid crystalline structurant lauric acid. Example L showed a noticeable shift to smaller particle size and higher reflectance compared to inventive example B, believed to be due in part to the smaller Petrolatum particles below 10 microns in size deleteriously affecting product appearance.

The aqueous base formula used for control example M without the Petrolatum preblend shows a particle size range 1 to 100 microns. These particles are believed to consist of individual or aggregated polymer and surfactant (e.g. SLES/copolymer) particles that did not completely disperse and/or dissolve. The addition of the Petrolatum preblend via injection process (example B) clearly shows a larger particle size distribution range of 100 to 1000 microns representative of the added Petrolatum particles.

TABLE 5

| Component | Wt. % | |
|---|---|---|
| | L | M |
| SLES (1) | 10.00 | 9.00 |
| CMEA (2) | 1.15 | 1.15 |
| Cocamidopropyl Betaine | 4.00 | 1.70 |
| Acrylate Copolymer (3) | 0 | 1.8 |
| Sodium Hydroxide | 0 | 0.1 |
| Lauric Acid | 3.1 | 0 |
| Soybean Oil | 3 | 0 |
| Petrolatum (6) | 3 | 0 |
| Glycerin | 1 | 0 |
| Guar Hydroxypropyltrimonium Chloride | 0.7 | 0 |
| Fragrance | 1 | 1 |
| Preservatives, others | 2 | 2 |
| Water | q.s. to 100 | q.s. to 100 |
| Reflectance (%) | 80.94 | 44.03 |

Process for making example L:
1. To main mix tank add 1383 parts of DI water and heat to 65 C
2. Add 150 parts White petrolatum, 165 parts lauric acid, 15 parts PEG 8 Stearate, 100 parts Cocamide MEA with mixing.
3. Heat to 80 C.
4. In a recirculation loop at a ratio of 3:1, inject 100 parts Cocamidopropyl betaine, 714 parts SLES 1 EO 70% at >65 C and mix 10 minutes.
5. Begin cooling to 35 C.
6. Inject 614 parts Cocamidopropyl betaine and 1328 parts DI water, mix 10 minutes.
7. Add 50 parts Glycerin
8. In a separate tank A add 100 parts DI water, 5 parts Citric Acid anhydrous and 2 parts Titanium Dioxide and mix until homogenous.
9. In a separate tank B add 150 parts Soybean oil and 35 parts Guar hydroxypropyltrimonium
10. Add the contents of tanks A and B to the main mix tank with recirculation.
11. Cool to <44 C 12. Add 9 parts DMDM Hydantoin, 6 parts Tetrasodium EDTA, 39% 0.5 parts Isostearic Acid, and 5 parts of color solution.
13. Add 65 parts of fragrance.
14. Continue recirculation for 20 minutes.

Example 4

Figure 4:
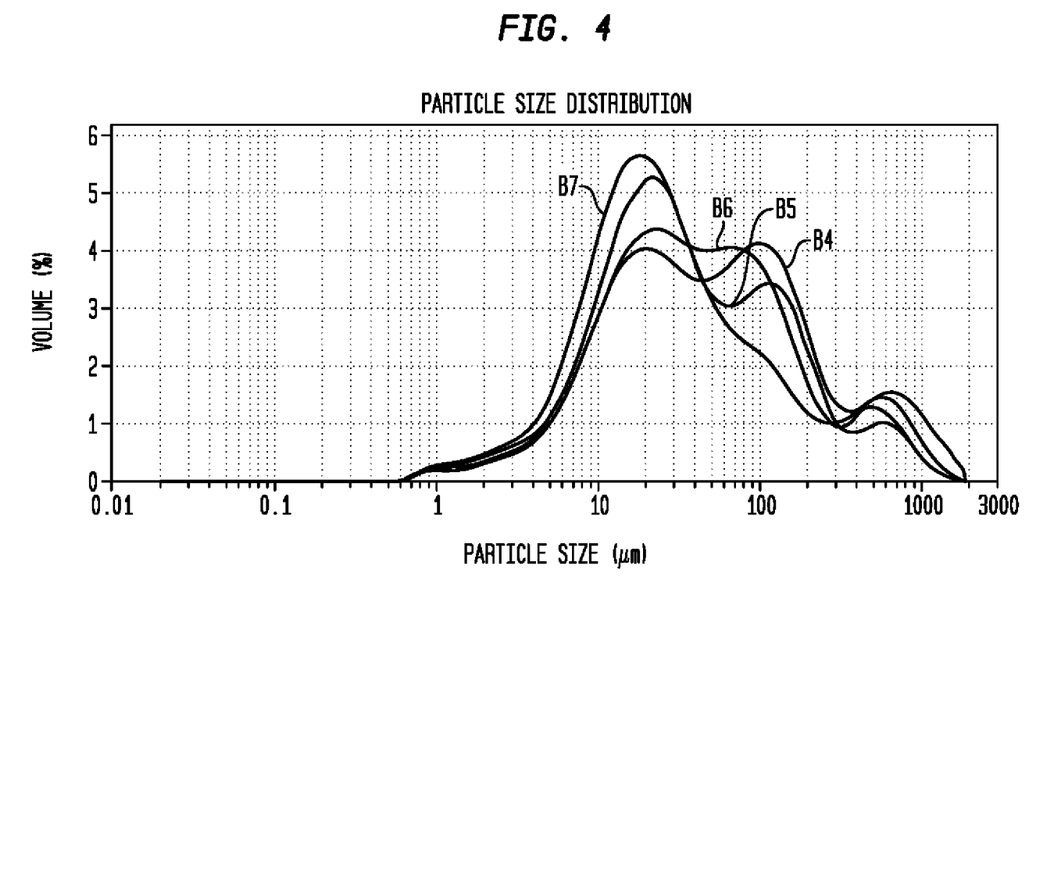
FIG. 4 is a graphical representation of the particle size distribution of Petrolatum droplets in inventive examples B4 to B7 described in example 4.
Figure 5:
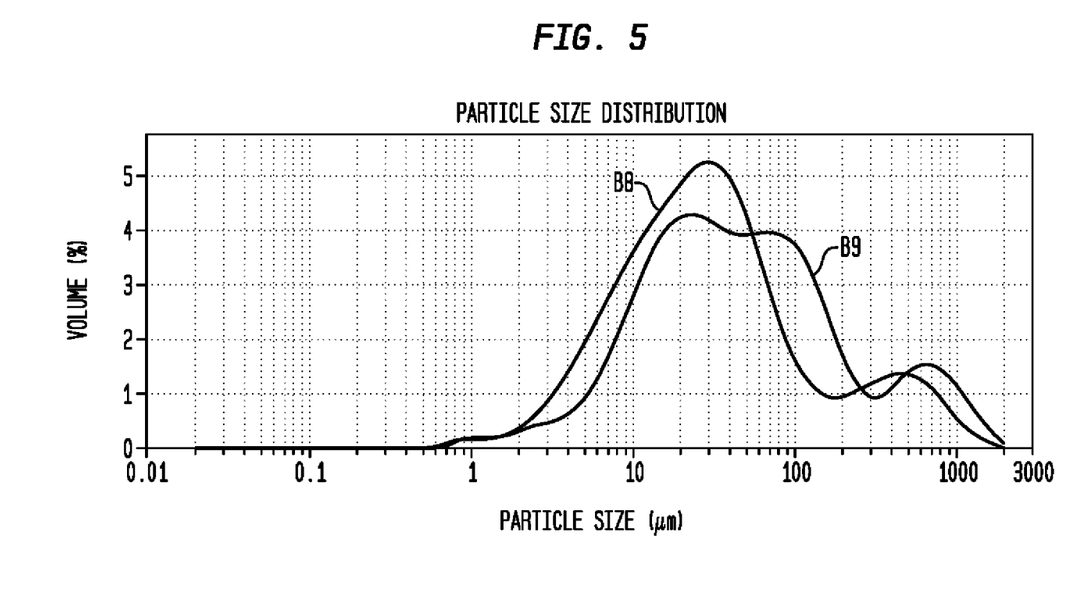
FIG. 5 is a graphical representation of the particle size distribution of Petrolatum droplets in inventive examples B8 and B9 described in example 4.

The effects of 1) aqueous and oil phase temperatures prior to blending and 2) oil phase flow rate (directly proportional to injection pressure) on particle size distribution of inventive example B was studied (see FIGS. 4 and 5). Particle size distribution was seen to vary within narrowly defined limits across the injection temperature and flow rates (pressures) studied.

More specifically, FIG. 4 compares results at 32 and 42 psig where the average particle size appears inversely proportional with pressure. FIG. 5 shows an overall increase in Petrolatum particle size at reduced aqueous base temperature, i.e. larger Petrolatum particles at 60 C vs. smaller Petrolatum particles at 65.5 C.

B4: Oil phase Temp 60 C, pressure at injection point 32 psig.
B5: Oil phase Temp 65.5 C, pressure at injection point 42 psig.
B6: Oil phase Temp 60 C, pressure at injection point 42 psig.
B7: Oil phase Temp 65.5 C, pressure at injection point 32 psig.
B8: Aqueous Base Temp 35 C, pressure at injection point 42 psig.
B9: Aqueous Base Temp 31 C, pressure at injection point 42 psig.
Samples B4 to B7; Aqueous Base Temp was 32 C
Samples B8 and B9; the Oil phase temp was 60 C Sample Preparation Method:
Examples A-K were prepared as follows:
1. Charge water into the mixing vessel and begin heating to 57.2 C.
2. Add Aqua SF-1 into main vessel.
3. Add Sodium Laureth Sulfate and Cocamide MEA into vessel and continue to heat to 76.7 C.
4. Add Tetrasodium EDTA into main beaker.
5. Add cocamidopropyl betaine into main vessel and continue to mix.
6. Add sodium hydroxide and neutralize to pH=6.1-6.5.
7. Add polypropylene glycol diluent to reduce viscosity.
8. Add preservative and perfume.
9. At 35 C, check product viscosity, appearance, consistency and add diluent as needed in order to attain desired viscosity.
10. Add Petrolatum (or other hydrophobic oil or fatty acid) into main beaker, while maintaining low mixing speed (<100 rpm) with an IKA® RW20 mixer (IKA Works, Inc., Germany); utilizing Lightnin® A320 mixer blades, until Petrolatum (or other hydrophobic oil or fatty acid) is uniformly dispersed.

Methods:
A) Reflectance Method
The Hunterlab Labscan XE spectrophotometer (Hunter Associates Laboratory, Inc., Reston, Va.) is used to determine product reflectance as follows:
1. Using the 2" port, standardize the equipment with both the standard black and white tiles.
2. Using approximately 50 g of product, fill the sample holder to a constant height for all samples.
3. Take measurement.
4. Repeat with multiple samples and average readings.

B) Particle Size Method:
Standard particle size (drop size) measurement protocol:
The particle size distribution of emollient oils in body wash prototype is characterized by light diffraction measurement using a Malvern Mastersizer® 2000 (Malvern Instruments, Malvern, UK) at ambient conditions. The raw data analysis is conducted by the Mastersizer 2000 software.

The preparation of samples is critical for light scattering measurement. Samples were pre-diluted with deionized water at a ratio of 1:1 to estimate actual shower conditions. The diluted sample was gently blended and loaded into dispersion chamber whereby a well dispersed sample containing representative Petrolatum and other particles was measured.

Experimental Procedure:
1. The Malvern sample dispersion accessories, optical unit and Mastersizer 2000 software are switched on in sequence.
2. Allow the system to automatically clean the sample dispersion accessory, align the optical system, measure the optical background, calculate the size distribution and save the records.
3. For each experiment, 10 experiment cycles are performed with 5 second delay between each cycle. The averaged results are reported
4. Set for normal sensitivity and irregular particle shape to calculate the drop size distribution. The refractive index of petrolatum is 1.4847 and water is 1.3300.
5. Add deionized water to clean the sample accessory until the laser signal intensity reaches 80% or above.
6. Add sample into the accessory until obscuration bar reaches mid value in green region. If sample is very viscous, pre-dispersion may be needed before adding to the accessory.
7. Perform the measurement.

C) Viscosity Measurement
This method covers the measurement of viscosity discussed herein. It is also used to measure the degree of structuring of the product.

Apparatus:
Brookfield RVT Viscometer;
Chuck weight and closer assembly for RV attachment;
RV-Spindle 5;
Plastic cups diameter greater than 2.5 inches Procedure:
1. Verify that the viscometer is level by referring to the bubble levels on the back of the instrument.
2. Connect the chuck/closer/weight assembly to the viscometer
3. Clean Spindle 5 with deionized water and pat dry with a Kimwipe® sheet. Slide the spindle in the closer and tighten.
4. Set the rotation speed at 20 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C. unless stated otherwise herein.
6. Lower the spindle into the product.
7. Start the viscometer.
8. Run the viscometer for 1 minute.
9. Multiply the dial readings by a factor of 2,000 and report viscosity readings in cps.

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A stable, multiphase isotropic cleansing composition, comprising:
   a. about 99 to 84 by wt. of an aqueous phase based on the total composition;
   b. about 1 to 16% by wt. of petrolatum having a melting point between 35 and 80 C and a minimum viscosity of 10 kPa-s to 10,000 cps at 32 C, wherein the concentration is based on the total composition;
   c. wherein the aqueous phase includes about 1 to 25% by wt. of a non-soap anionic surfactant based on the total composition;
   d. wherein the aqueous phase contains about 0.5 to 10% by wt. of total polymeric dispersion stabilizing agent(s) based on the total composition;
   e. less than about 2% by wt. of total hydrophobic glyceride(s), hydrocarbon(s) excluding petrolatum, silicone oils, or blends and derivatives thereof based on the total composition;
   f. less than about 1.5% by wt. of total liquid crystalline structurant(s), crystalline hydroxyl-containing stabilizer(s), C10-C22 ethylene glycol fatty acid ester(s), silica(s), clay(s) or blends thereof based on the total composition; and
   g. wherein the cleansing composition has a maximum reflectance of 80% as measured by the standard reflectance method and wherein greater than 50% by volume of the petrolatum particles have a diameter greater than 100 microns as measured by the standard particle size method.

2. The cleansing composition of claim 1 wherein the composition contains only an aqueous and an oil phase.

3. The cleansing composition of claim 1 wherein the composition contains about 2.5 to 12% by wt. of a non-soap anionic surfactant based on the total composition.

4. The cleansing composition of claim 1 wherein the non-soap anionic surfactant includes C8 to C18 acyl isethionate(s).

5. The cleansing composition of claim 4 wherein the $C_8$-$C_{18}$ acyl isethionate(s) are prepared by reaction between alkali metal isethionate with mixed aliphatic fatty acids having from 6 to 18 carbon atoms and an iodine value of less than 20.

6. The cleansing composition of claim 5 wherein at least 75% of the mixed fatty acids have from 12 to 18 carbon atoms and up to 25% have from 6 to 10 carbon atoms.

7. The cleansing composition of claim 1 wherein the composition contains about 2.5 to 8% by wt. of Petrolatum based on the total composition.

8. The cleansing composition of claim 1 wherein the aqueous phase contains about 1 to 8% by wt. of total polymeric dispersion stabilizing agent(s) based on the total composition.

9. The cleansing composition of claim 1 wherein the polymeric dispersion agents are selected from carbohydrate gums, acrylate containing homo and copolymers or blends thereof.

10. The cleansing composition of claim 9 wherein the carbohydrate gums are selected from Hydroxypropyl Methylcellulose, Sodium Hydroxypropyl starch phosphate and Xanthan Gum or blends thereof.

11. The cleansing composition of claim 9 wherein the acrylate containing homo and copolymers are selected from crosslinked poly acrylates, hydrophobically modified cross linked polyacrylates, alkali swellable acrylic latex polymers or blends thereof.

12. The cleansing composition of claim 11 wherein the polymeric dispersion agents includes hydrophobically modified cross linked polyacrylates.

13. The cleansing composition of claim 1 wherein the total hydrophobic glyceride(s), hydrocarbon(s) excluding petrolatum, or silicone oils or blends and derivatives thereof is less than about 1.5% by wt. based on the total composition.

14. The cleansing composition of claim 1 wherein the total liquid crystalline structurant(s), crystalline hydroxyl-containing stabilizer(s), C10-C22 ethylene glycol fatty acid ester(s), silica(s), clay(s) or blends thereof is less than about 0.5% by wt. based on the total composition.

15. The cleansing composition of claim 1 wherein the cleansing composition has a maximum reflectance of 70% as measured by the standard reflectance method.

16. The cleansing composition of claim 1 wherein there is no observed phase separation after 3 months at storage temperatures of either 45 C, 37 C, 25 C, or 4 C, or after storage for 2 weeks at 50 C.

17. The cleansing composition of claim 1 further comprising one or more polyhydric alcohol(s), polyol(s) or blends thereof.

18. The cleansing composition of claim 1 further comprising one or more higher fatty acids selected from lauric, myristic, palmitic, stearic, behenic, oleic, linoleic, linolenic, lanolic, isostearic, arachidonic or blends thereof.

* * * * *